United States Patent [19]
Isomura et al.

[11] Patent Number: 6,071,554
[45] Date of Patent: Jun. 6, 2000

[54] PROCESS FOR FORMING ELECTRODE FOR CERAMIC SENSOR ELEMENT BY ELECTROLESS PLATING

[75] Inventors: Hiroshi Isomura, Komaki; Yukichika Ito, Iwakura; Akio Mizutani, Nagoya; Nobuhiro Hayakawa, Chita, all of Japan

[73] Assignee: NGK Spark Plug Co., Ltd., Nagoya, Japan

[21] Appl. No.: 09/199,551

[22] Filed: Nov. 25, 1998

[30]   Foreign Application Priority Data

Nov. 25, 1997 [JP] Japan .................................. 9-323289

[51] Int. Cl.⁷ ........................................................ B05D 5/12
[52] U.S. Cl. ........................ 427/125; 427/230; 427/443.1
[58] Field of Search ..................... 204/427, 424; 106/1.24, 1.28; 427/58, 125, 443.1, 230

[56]   References Cited

U.S. PATENT DOCUMENTS

| | | | |
|---|---|---|---|
| 4,650,697 | 3/1987 | Kitagawa et al. | ....................... 427/128 |
| 5,948,225 | 9/1999 | Katafuchi et al. | ...................... 204/421 |

*Primary Examiner*—Brian K. Talbot
*Attorney, Agent, or Firm*—Morgan, Lewis & Bockius LLP

[57]   ABSTRACT

Disclosed is a process for the formation of an electrode for sensor element which comprises the formation of a platinum electrode on a solid electrolyte formed in a predetermined shape as a sensor element by electroless plating, wherein said electroless plating is effected in a platinum (II) complex solution as a plating solution on which a reducing agent for reducing said platinum (II) complex is acted.

8 Claims, 4 Drawing Sheets

< EXAMPLE 1 >

< COMPARATIVE EXAMPLE 1 >

< EXAMPLE 1 >

NO AMMONIUM CHLORIDE ADDED

< EXAMPLE 2 >

AMMONIUM CHLORIDE ADDED

< COMPARATIVE EXAMPLE 1 >

TETRAVALENT PLATINUM AMMINE

< COMPARATIVE EXAMPLE 2 >

1% DICHLORODIAMMINE PLATINUM ADDED

PROCESS FOR FORMING ELECTRODE FOR CERAMIC SENSOR ELEMENT BY ELECTROLESS PLATING

FIELD OF THE INVENTION

The present invention generally relates to a process for formation of an electrode for ceramic element by electroless plating, particularly to the process which comprises formation of a platinum electrode on a solid electrolyte ceramic body, and more specifically to the process for uniformly forming the platinum electrodes inside and outside of an oxygen ion conductive solid electrolyte ceramic body formed in a predetermined shape such a thimble-shape for a gas sensor element (e.g., an oxygen sensor element, an humidity sensor and an NOx sensor element) by electroless plating (or rather electroless deposition).

BACKGROUND OF THE INVENTION

The production of an oxygen sensor element for and a A/F sensor for instance to be used in an exhaust gas stream, has heretofore been accomplished by a process involving the following steps of:

(1) forming a thin platinum layer for an oxygen detection electrode by electroless plating on the exterior of a zirconia ceramic formed in a cup or thimble-shape;

(2) enhancing the denseness of the detection electrode by applying a heat;

(3) forming a ceramic protective layer on the entire surface of the detection electrode for protecting the detection electrode;

(4) forming another thin platinum layer for a reference electrode by electroless plating in the interior of the cup-shaped zirconia ceramic; and (5) aging the element in an atmosphere of a high temperature exhaust gas where the sensor is used.

The thin platinum layers for the detection and reference electrodes are formed by electroless plating. In this electroless plating, a solution of tetravalent platinum having a six-coordinate octahedral structure represented by hexaammine platinum (IV) tetrachloride ($[Pt(NH_3)_6]Cl_4$) has been used. This complex has been reduced by a reducing agent to allow platinum to be deposited to a small thickness.

However, the inventors of the present invention think that since the hexaammine platinum (IV) tetrachloride has ligands as many as six and a stereostructure of octahedron, the ammine can be easily replaced by other ligands (e.g., chlorine) becoming impurities having other polygonal structures, making it difficult to remove the impurities and obtain a high purity product. If such impurities are present, their effect changes a metal deposition rate in the electroless plating, giving a tendency that the thickness of the thin platinum metal layer thus obtained can not be uniform i.e. partly great or small in the layer thickness. Further, when the production is subjected to a mass production basis, there appears a tendency that the layer thickness varies from lot to lot. In particular, the oxygen sensor elements formed in the cup-shape (or one-end closed cylinder shape) would show that the thickness of the thin platinum layer particularly inside the cup—cup shaped element, varies from an open end portion through a central portion to the closed end portion exhibiting different sensor properties and making it difficult to mass-produce sensor elements with a stable and high quality.

It is thought by the inventors of the present inventions that tetravalent platinum follows a reaction path involving the change of the valence of platinum ($4 \rightarrow 2 \rightarrow 0$) until it is deposited. It is likely therefor that the impurities would be produced when the tetravalent platinum changes its valence from 4 to 2. Thus, even if the tetravalent platinum has a high purity, the impurities can be present at the reaction process, making it difficult to mass-produce the sensor elements with the stable and high quality.

The present invention has been worked out to solve the foregoing problems found by the inventors.

SUMMARY OF THE INVENTION

An object of the present invention is therefor to provide a process for formation of an electrode for a sensor element which allows a mass production of the sensor elements provided with an electrode having a stable and high quality in terms of thickness and resistivity of the electrode.

The present invention particularly concerns a process for forming an electrode for a gas sensor element, which process comprises formation of a platinum electrode on an oxygen-ion conductive solid electrolyte ceramic body formed in any predetermined shape by electroless plating. One of the features of the method is characterized in that said electroless plating is effected in a platinum (II) complex solution as a plating solution on which a reducing agent for reducing said platinum (II) complex is acted, thereby improving a uniformity of thickness and resistivity of the resultant platinum electrode formed on the ceramic body.

This process for electroless plating according to the invention is especially useful in forming a uniform thickness of a platinum electrode layer inside a thimble-shaped (or rather cup-shaped or one end closed tubular or cylindrical shaped) ceramic body that is made of oxygen ion conductive solid electrolyte such as zirconia for a gas sensor cell element, in such a method that an electroless plating liquid is poured inside the thimble-shaped ceramic body having a hollow formed therein.

DETAILED DESCRIPTION OF THE INVENTION

Figure 1:
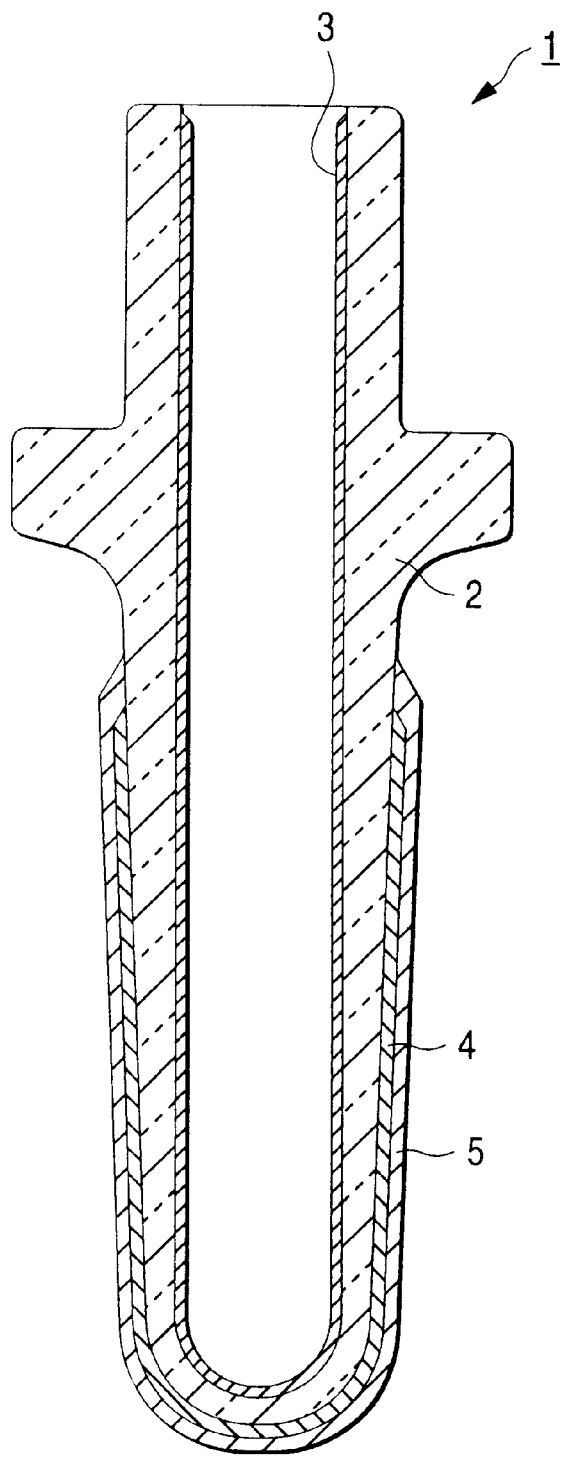
FIG. 1 is a sectional view of an oxygen sensor element having two electrodes, the one formed inside and the other outside a thimble-shaped solid electrolyte ceramic body

The solid electrolyte formed in a predetermined shape as a sensor element may be in any form such as a bag, plate tube and cylinder so far as it has a hollow inside and is opened at one end but closed at the other. As the material of solid electrolyte there may be used a zirconia ceramic partially stabilized by yttria or calcia.

In the process for formation of the electrode for the sensor element according to the present invention, a solution of a platinum (II) complex is used as an electroless plating solution(or liquid) The platinum (II) complex, i.e., divalent platinum complex has a four-coordinate planar structure. Thus, as compared with a platinum (IV) complex having a six-coordinate octahedral structure, i.e., tetravalent platinum complex, the platinum (II) complex has a small number of ligands and a planar structure and thus is little subject to replacement of ligands by other ligands, preventing impurities from entering, and hence making it easy to obtain a high purity product having a uniform electrode. This plating solution forms a thin platinum layer on any ceramic body when acted on by a reducing agent for reducing divalent platinum (e.g., hydrazine, sodium borohydride). Since this plating system is little subject to entrance of impurities, the metal deposition rate is stabilized. Therefore, the thickness of the thin platinum layer is almost uniform all over the entire surface of the sensor electrode. Further, when the sensors are mass-produced, the sensors have almost uniform electrode layer thickness from lot to lot. Accordingly, sensors thus mass-produced are almost uniform in properties such as sheet resistivity (i.e. resistivity measured across the inside electrode portion formed from the closed end to the open end of the sensor electrolyte) and internal resistivity i.e. resistivity measured between an outside electrode/or rather a detection electrode and an inside electrode/or rather a reference electrode, the internal resistivity being determined when the atmosphere of an exhaust gas in which the sensor is placed is shifted fuel-rich. Thus, an advantage or effect of mass-production sensors with a stable and high quality can be exerted.

The plating conditions may be properly predetermined depending on the thickness of the platinum layer to be formed and thus not specifically limited. In practice, however, the concentration of platinum in the plating solution is predetermined to a range of from 10 to 20 g/l, preferably from 13 to 15 g/l. The plating temperature is predetermined to a range of from 60 to 90° C., preferably from 70 to 85° C. The pH value of the plating solution is predetermined to a range of from 8 to 14, preferably from 10 to 13. The processing time is predetermined to a range of from 100 to 200 minutes, preferably from 140 to 180 minutes.

In the platinum (II) complex of the present invention, all of the four ligands are preferably the same because such a structure produces no geometrical isomers such as cis-form and trans-form. Examples of such a platinum (II) complex include tetranitroplatinum (II) complex ($[Pt(NO_2)_4]^{2+}$), tetrachloroplatinum (II) complex ($[PtCl_4]^{2+}$), and tetraammine platinum (II) complex ($[Pt(NH_3)_4]^{2+}$). Preferred among these platinum (II) complexes is tetraammine platinum (II) complex because it is easy to handle, has a high water solubility and can provide a proper deposition rate that prevents forming unevenness in the thin platinum layer and hence makes it easy to give uniform layer thickness.

Further, the tetraammine platinum (II) complex has a purity of not less than 99% (the term "purity" as used herein indicates % by weight of tetraammine platinum (II) complex based on the total weight of platinum (II) complex), or preferably not less than 99.5% to further uniformalize the layer thickness.

Moreover, if electroless plating is effected in, as a plating solution, the tetraammine platinum (II) complex solution comprising an ammonium salt is incorporated therein, the deposition rate can be adjusted to change slowly, making it to further uniformalize the layer thickness to advantage. This mechanism is thought as follows. The reduction of tetraammine platinum (II) complex causes production of platinum having a valence of 0 and an ammonium salt derived from ammine as ligand. However, it is thought that if this ammonium salt has previously been allowed to exist in the reaction system, the rapid initiation of reaction is prevented.

The amount of the ammonium salt to be incorporated is not specifically limited. In practice, however, it is preferably from 5 to 15% by weight. If the amount of the ammonium salt to be incorporated falls below 5% by weight, the effect of slowing down the deposition rate cannot be sufficiently exerted. On the contrary, if the amount of the ammonium salt to be incorporated exceeds 15% by weight, the resulting deposition rate is too slow for practical use.

Preferred examples of the present invention will now be described hereinafter.

EXAMPLE 1

This will be described with reference to an oxygen sensor element. The oxygen sensor element is disposed in an oxygen sensor mounted in an exhaust pipe for controlling the air-fuel ratio (A/F) of an internal combustion engine to measure the oxygen concentration in the gas (exhaust gas) to be measured. As shown in FIG. 1, the oxygen sensor element 1 comprises a solid electrolyte body 2 made of zirconia ceramic formed in the shape of cup (closed-end cylinder). Formed on the inner wall of the solid electrolyte 2 is a reference electrode 3 made of platinum exposed to the atmosphere. On the other hand, formed on the outer surface of the solid electrolyte 2 is a detection electrode 4 made of platinum exposed to the gas to be detected or measured. Further, the surface of the detection electrode 4 is covered by a porous ceramic protective layer 5 for protecting the detection electrode 4 against toxic substances of the gas.

The oxygen sensor element of FIG. 1 is firstly prepared as follows. In detail, 100 mols of $ZrO_2$ having a purity of not less than 99% are blended with 5 mols of $Y_2O_3$ having a purity of not less than 99% in a wet process, and then calcinated at a temperature of 1,300° C. To the material thus calcinated is then added water. The material is then ground by a ball mill. To the material thus ground is then added a water-soluble binder and then spray-dried to undergo granulation. The material thus granulated is pressed to form a cup or rather a thimble shape (closed-end cylinder) by a rubber press process, and then ground by a whetstone to have a predetermined shape having a central bulging flange outside and a hollow inside. Subsequently, this cup-shaped green body is sintered at a temperature of 1,500° C. for 3 hours to obtain a zirconia ceramic corresponding to the solid electrolyte ceramic body 2 having the thimble-shape with the length of about 5 cm and the thickness of about 1–2 mm slanting from the closed end to the open end.

A thin platinum layer is then formed on the exterior of the foregoing solid electrolyte 2 to a thickness of from 1 to 2 $\mu$m by partly submerging the electrolyte 2 and electroless platinum plating thereon to obtain a detection electrode 4. In some detail, the solid electrolyte 2 is treated in a 70° C. aqueous solution of $[Pt(NH_3)_4]Cl_2$ (purity: not less than 99%) having a platinum content of 13 g/liter as a plating solution with an aqueous solution of hydrazine as a reducing agent at a pH value of from 10 to 13 for 140 minutes, washed with water, and then dried to form the thin platinum layer having a thickness of from 1 to 2 $\mu$m.

Thereafter, this thin platinum layer is subjected to heat treatment at a temperature of 1,200° C. in the atmosphere for 90 minutes to enhance the denseness of the thin platinum layer constituting the detection electrode 4. Subsequently, in order to protect the foregoing detection electrode 4, a spinel powder is plasma-spray coated onto the entire surface of the detection electrode 4 to form a ceramic protective layer 5 having a thickness of from 50 to 150 µm thereon.

Thereafter, another thin platinum layer is formed on the inner wall surface of the solid electrolyte 2 to a thickness of from 1 to 2 µm by pouring electroless platinum plating solution into a hollow formed in the electrolyte 2 to obtain a reference electrode 3 by electroless plating. In more detail, the solid electrolyte 2 is treated in a 85° C. with the electroless plating solution of [Pt(NH$_3$)$_4$]Cl$_2$ (purity: not less than 99%) having a platinum content of 15 g/liter as a plating solution with an aqueous solution of hydrazine as a reducing agent at a pH value of from 10 to 13 for 180 minutes, washed with water, and then dried to form the thin platinum layer having a thickness of from 1 to 2 µm.

Subsequently, the air-fuel ratio detection element 1 is subjected to ageing in an atmosphere of exhaust gas so that the detection electrode 4 is stabilized.

EXAMPLE 2

Since this example 2 was effected in the same manner as in Example 1 previously described except that a different electroless platinum plating process is used, it will be described with reference only to the difference of the electroless platinum plating process for formation of the reference electrode 3. Namely, the solid electrolyte 2 of Example 2 is treated in a 85° C. aqueous solution of [Pt(NH$_3$)$_4$]Cl$_2$ (purity: not less than 99%) having a platinum content of 15 g/liter and containing ammonium chloride in an amount of 10% by weight based on the weight of platinum as a plating solution with an aqueous solution of hydrazine as a reducing agent at a pH value of from 10 to 13 for 180 minutes, washed with water, and then dried to form a thin platinum layer having a thickness of from 1 to 2 µm.

COMPARATIVE EXAMPLE 1

Since this comparative example is effected in the same manner as in Example 1 except that a different electroless platinum plating process is used, it will be described with reference only to the difference of the electroless platinum plating process for formation of the reference electrode 3. Namely, the solid electrolyte 2 is treated in a 85° C. aqueous solution of [Pt(NH$_3$)$_6$]Cl$_4$ (hexaammine platinum (IV) tetrachloride) having a platinum content of 13 g/l as a plating solution with an aqueous solution of hydrazine as a reducing agent at a pH value of from 10 to 13 for 180 minutes, washed with water, and then dried to form a thin platinum layer having a thickness of from 1 to 2 µm.

COMPARATIVE EXAMPLE 2

Since this comparative example 2 was effected in the same manner as in Example 1 except that a different electroless platinum plating process is used, it will be described with reference only to the difference of the electroless platinum plating process for formation of the reference electrode 3. Namely, the solid electrolyte 2 is treated in a 85° C. aqueous solution of [Pt(NH$_3$)$_4$]Cl$_2$ (tetraammine platinum (II) dichloride; purity: not less than 99%) having a platinum content of 15 g/l and containing [Pt(NH$_3$)$_2$Cl$_2$]Cl$_2$ (dichlorodiammine platinum (II) dichloride) incorporated therein as impurities in an amount of 1% by weight based on the total weight thereof as a plating solution with an aqueous solution of hydrazine as a reducing agent at a pH value of from 10 to 13 for 180 minutes, washed with water, and then dried to form the thin platinum layer having a thickness of from 1 to 2 µm.

Figure 2A:
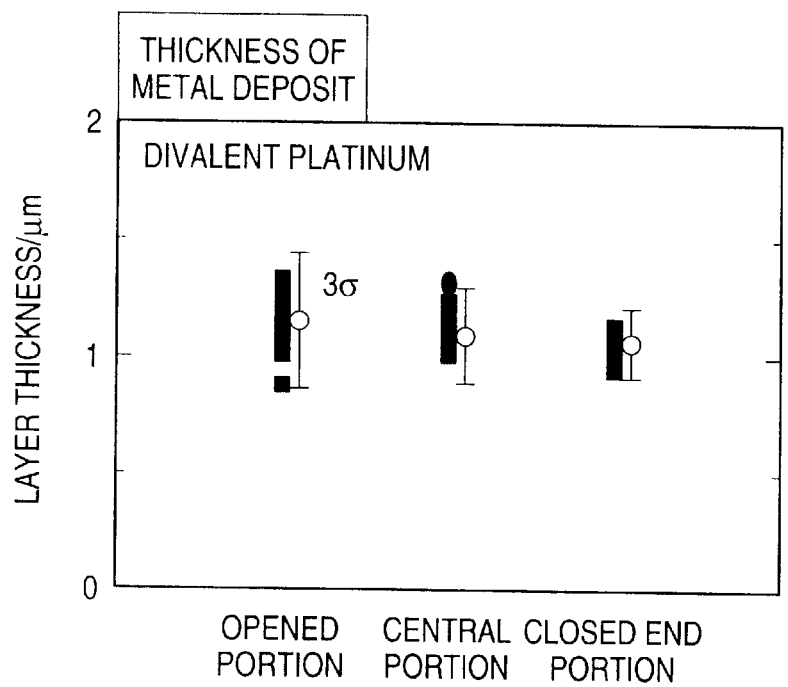
FIG. 2A is a graph illustrating a distribution of measured thickness of platinum metal layer deposited at various points in Example 1 made by applying the process of the present invention.
Figure 2B:
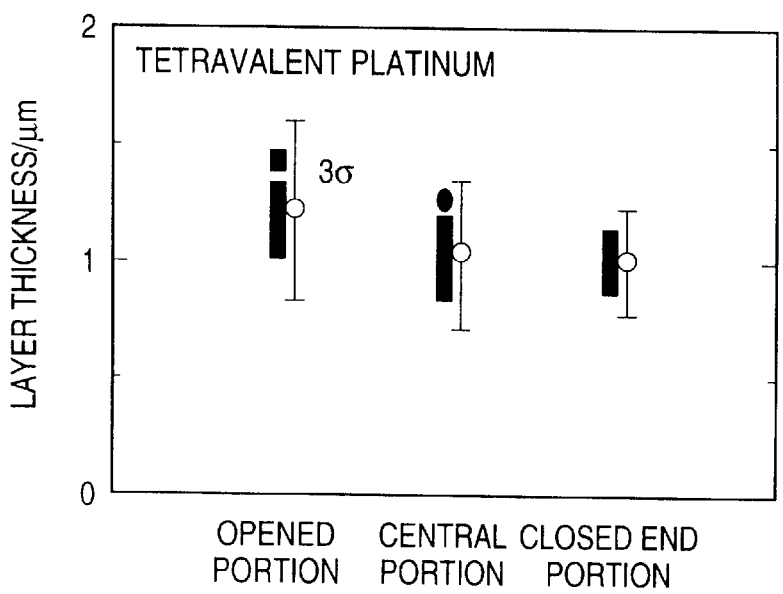
FIG. 2B is a graph illustrating the distribution of the thickness of platinum metal layer deposited at various points in Comparative Example 1.
Figure 3A:
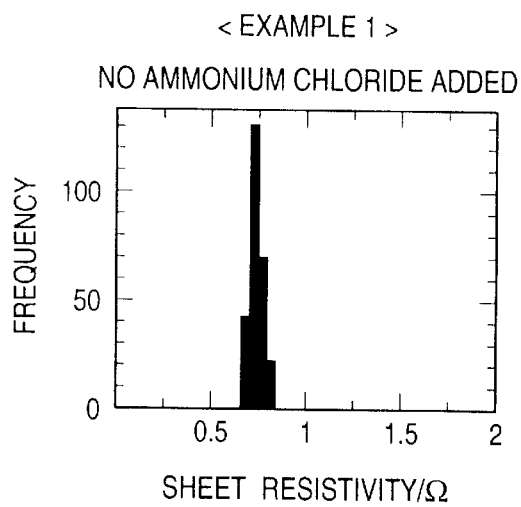
FIG. 3A is a graph illustrating the distribution of a sheet resistivity of the Example 1 made by applying the process of the present inventions.
Figure 3B:
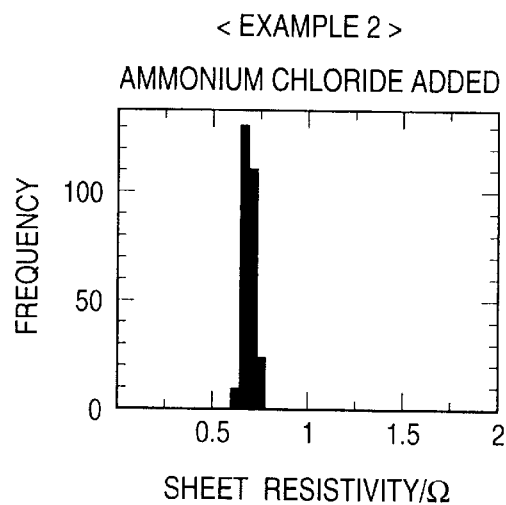
FIG. 3B is a graph illustrating the distribution of the sheet resistivity of Example 2 made by applying the process of the present inventions.
Figure 3C:
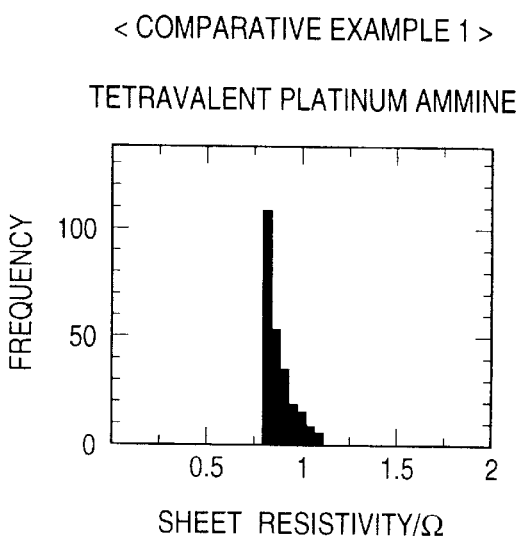
FIG. 3C is a graph illustrating the distribution of the sheet resistivity of the Comparative Example 1.
Figure 3D:
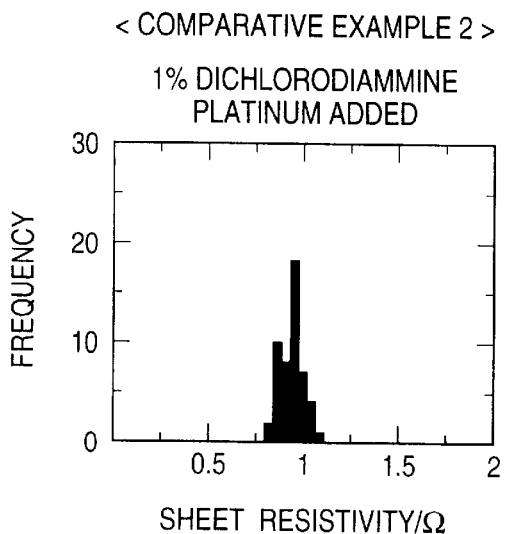
FIG. 3D is a graph illustrating the distribution of the sheet resistivity of Comparative Example 2.

TEST EXAMPLE 40 samples were prepared for each of the oxygen sensor elements previously explained as in Example 1 and Comparative Example 1. These samples were each cut vertically into halves. The section of the sample is then subjected to fluorescent X-ray analysis to determine the thickness variation of the platinum metal deposits formed on the inner reference electrode 3 at three points, i.e., open end portion 3a, central portion 3b and closed end portion 3c. The results are set forth in FIGS. 2A and 2B and Table 1. The results give the following two findings. As compared with comparative example 1, Example 1 shows a small scattering in the thickness variation of the metal deposits within the range of from the open end to the closed end through the central portion and hence approximately uniform layer thickness all over this range in one unit of the oxygen sensor element. Further, Example 1 exhibits a smaller triple standard deviation value (3 σ) of layer thicknesses and hence a smaller scattering in the layer thickness from lot to lot than Comparative Example 1.

TABLE 1

|  | Example 1 | | | Comparative Example 1 | | |
| --- | --- | --- | --- | --- | --- | --- |
|  | Open end portion | Central portion | Closed end portion | Open end portion | Central portion | Closed end portion |
| Average thickness (µm) at various portions | 1.16 | 1.11 | 1.08 | 1.24 | 1.06 | 1.03 |
| Triple of standard deviation of layer thickness (= 3σ) | 0.287 | 0.210 | 0.145 | 0.386 | 0.320 | 0.232 |
| Scattering in layer thickness over entire portion (µm) *1) |  | 0.08 |  |  | 0.21 |  |

*1) The scattering in the layer thickness over the entire portion is the difference in the average layer thickness between at the greatest thickness portion and at the smallest thickness portion.

The oxygen sensor elements of Examples 1 and 2 and Comparative Examples 1 and 2 were then examined for sheet resistivity (i.e. resistance measured across the portion between the closed end and open end of the sensor) as one of the sensor properties. The results are set forth in FIGS. 3A to 3D and Table 2. The results show that as compared with the sensor products of the comparative examples, those of the examples according to the present invention exhibit a small sheet resistivity in terms of mean value and a small standard deviation (σ) of sheet resistivity, which gives a small scattering in sheet resistivity from lot to lot, providing good sensor properties.

TABLE 2

|  | Example 1 | Example 2 | Comparative Example 1 | Comparative Example 2 |
|---|---|---|---|---|
| Sheet resistivity (Ω) | 0.69 | 0.65 | 0.73 | 0.91 |
| Standard deviation (σ) | 0.04 | 0.03 | 0.07 | 0.07 |

Figure 4:
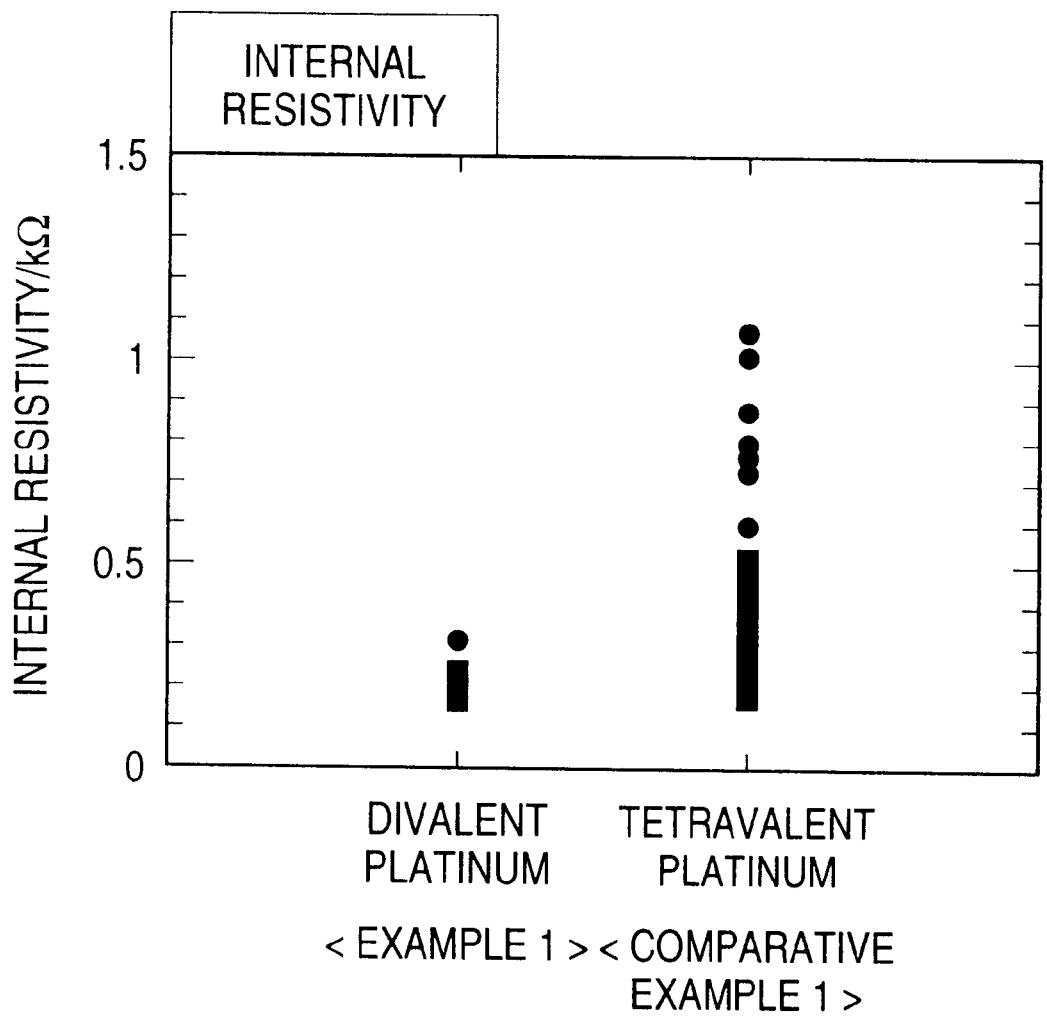
FIG. 4 is a graph comparatively illustrating the distribution of the internal resistivity of the inside electrode layer of Example 1 and that distribution of the Comparative Example 1.

Further, the products of Example 1 and Comparative Example 1 were examined for internal resistivity (i.e. resistance measured across the portions between the detection electrode and the reference electrode when the atmosphere of exhaust gas is rich). The results are set forth in FIG. 4. As compared with Comparative Example 1, Example 1 shows a small scattering in internal resistivity and thus exhibits good sensor properties.

The foregoing test results were made on the reference electrode 3, i.e., inner platinum layer, because the uniformity of the electrode layer formed on the inner wall of the thimble-shaped ceramic is critical and not easily obtained. Notwithstanding, the method of this invention is applicable to the detection electrode 4, i.e., outer platinum layer to obtain the similar improvements.

The embodiments of implication of the present invention are not limited to the foregoing embodiments (examples). It goes without saying that the present invention may be in various forms so far as it falls within the technical scope thereof.

What is claimed is:

1. A process for forming an electrode for sensor element, which comprises formation of a platinum electrode on a solid electrolyte body formed in a predetermined shape as a sensor element by electroless plating, wherein said electroless plating is effected in a platinum (II) complex solution as a plating solution on which a reducing agent for reducing said platinum (II) complex is acted.

2. The process for the formation of an electrode for sensor element according to claim 1, wherein said platinum (II) complex is a tetraammine platinum (II) complex.

3. The process for the formation of an electrode for sensor element according to claim 2, wherein said tetraammine platinum (II) complex has a purity of not less than 99%, in which the term "purity" as used herein is meant to indicate % by weight of tetraammine platinum (II) complex based on the total weight of platinum (II) complex.

4. The process for the formation of an electrode for sensor element according to claim 2, wherein said electroless plating is effected in, as a plating solution, a tetraammine platinum (II) complex solution comprising an ammonium salt to be produced when said tetraammine platinum (II) complex is reduced, on which said reducing agent is acted.

5. The process for the formation of an electrode for sensor element according to claim 3, wherein said electroless plating is effected in, as a plating solution, a tetraammine platinum (II) complex solution comprising an ammonium salt to be produced when said tetraammine platinum (II) complex is reduced, on which said reducing agent is acted.

6. The process for the formation of an electrode for sensor element according to claim 4, wherein the added amount of said ammonium salt is from 5 to 15% by weight based on the weight of platinum.

7. The process for the formation of an electrode for sensor element according to claim 5, wherein the added amount of said ammonium salt is from 5 to 15% by weight based on the weight of platinum.

8. The process for the formation of the electrode for sensor element according to claim 1, claim 2 or claim 3, further comprising the step of;

pouring an elecroless plating solution into an hollow formed in the solid electrolyte ceramic body in a shape of a thimble; and forming a uniform thickness of an platinum electrode layer on an inner wall of the hollow from a open end to the closed end of the thimble shaped electrolyte ceramic body resulting in that a thickness uniformity of the formed platinum electrode layer is less than about 0.12 (μm) determined based on the thickness of the electrode layer scattered on the inner wall by the average layer thickness difference between the greatest and smallest electrode thickness portions spaced apart at least about 20 mm.

* * * * *